(12) United States Patent
Minato et al.

(10) Patent No.: US 7,118,557 B2
(45) Date of Patent: Oct. 10, 2006

(54) DISPOSABLE DIAPER

(75) Inventors: Hironao Minato, Kagawa-ken (JP); Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 380 days.

(21) Appl. No.: 10/664,906

(22) Filed: Sep. 22, 2003

(65) Prior Publication Data
US 2004/0059311 A1    Mar. 25, 2004

Related U.S. Application Data

(62) Division of application No. 09/220,889, filed on Dec. 28, 1998, now Pat. No. 6,659,993.

(30) Foreign Application Priority Data
Dec. 26, 1997    (JP)    ................... 9-359098

(51) Int. Cl.
A61F 13/494    (2006.01)
A61F 13/475    (2006.01)
A61F 13/476    (2006.01)

(52) U.S. Cl. ............... 604/385.27; 604/385.28

(58) Field of Classification Search ...............
604/385.24–385.3, 385.2, 385 A
See application file for complete search history.

(56) References Cited

U.S. PATENT DOCUMENTS

| | | | | |
|---|---|---|---|---|
| 4,300,562 A | * | 11/1981 | Pieniak | 604/385.26 |
| 4,636,207 A | * | 1/1987 | Buell | 604/370 |
| 4,695,278 A | | 9/1987 | Lawson | |
| 4,704,116 A | | 11/1987 | Enloe | |
| 4,795,454 A | * | 1/1989 | Dragoo | 604/385.28 |
| 4,816,025 A | | 3/1989 | Foreman | |
| 4,904,251 A | | 2/1990 | Igaue et al. | |
| 5,061,261 A | | 10/1991 | Suzuki et al. | |
| 5,114,420 A | | 5/1992 | Igaue et al. | |
| 5,246,432 A | | 9/1993 | Suzuki et al. | |
| 5,403,301 A | * | 4/1995 | Huffman et al. | 604/385.28 |
| 5,454,803 A | * | 10/1995 | Sageser et al. | 604/385.28 |
| 5,571,096 A | | 11/1996 | Dobrin et al. | |
| H001630 H | | 1/1997 | Roe et al. | |
| 5,624,424 A | * | 4/1997 | Saisaka et al. | 604/385.28 |
| 5,624,426 A | | 4/1997 | Roe et al. | |
| 5,653,843 A | * | 8/1997 | Fell et al. | 156/265 |
| 5,674,213 A | | 10/1997 | Sauer | |
| 6,123,694 A | | 9/2000 | Pieniak et al. | |

(Continued)

FOREIGN PATENT DOCUMENTS

DE    3423644 A1    1/1986

(Continued)

OTHER PUBLICATIONS

English Language Abstract of JP 10 290817.

(Continued)

*Primary Examiner*—Karin Reichle
(74) *Attorney, Agent, or Firm*—Lowe Hauptman & Berner LLP

(57) ABSTRACT

A disposable diaper includes a liquid-impermeable topsheet, a liquid-permeable backsheet and an absorbent core therebetween. A pair of barrier cuffs which are elastically extendable in a longitudinal direction of the diaper are provided along transversely opposite side flaps of the diaper. Front and rear ends of the barrier cuffs are bonded to the diaper at longitudinally opposite ends thereof. Outer side edges of the barrier cuffs are bonded to outer edges of the flaps and inner side edges of the barrier cuffs are bonded to the flaps along lines defined between the outer side edges and transversely opposite side edges of the core.

3 Claims, 3 Drawing Sheets

U.S. PATENT DOCUMENTS 6,659,993 B1 * 12/2003 Minato et al. ......... 604/385.27

FOREIGN PATENT DOCUMENTS

| DE | 3741828 C1 | 5/1989 |
|----|------------|--------|
| EP | 0 329 160 | 8/1989 |
| EP | 0745367 A2 | 12/1996 |
| FR | 2 699 813 | 7/1994 |
| GB | 2 215 986 | 6/1992 |
| GB | 2 280 593 | 2/1995 |
| JP | 64-18105 | 1/1989 |
| JP | 2-71521 U | 5/1990 |
| JP | 3-268753 | 11/1991 |
| JP | 4-12256 | 4/1992 |
| JP | 4-55072 | 9/1992 |
| JP | 4-295356 | 10/1992 |
| JP | 4-325153 | 11/1992 |
| JP | 617726 U | 3/1994 |
| WO | WO 97/16144 | 5/1997 |

OTHER PUBLICATIONS

English Language Abstract of JP 03 222946.
European Search Report and Annex.

* cited by examiner

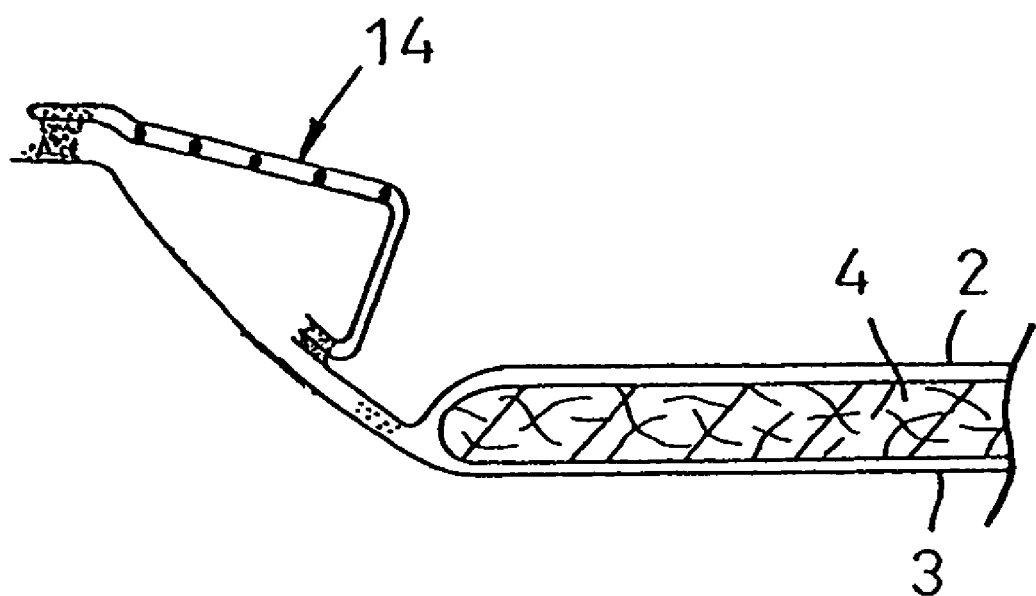

US 7,118,557 B2

DISPOSABLE DIAPER

This application is a divisional application of U.S. patent application Ser. No. 09/220,889 filed Dec. 28, 1998, now U.S. Pat. No. 6,659,993, which is incorporated herein by reference in its entirety.

BACKGROUND OF THE INVENTION

This invention relates to a disposable diaper having a high ventilation property.

A disposable diaper described in Japanese Utility Model Application Disclosure Gazette (Kokai) No. Sho64-18105 includes a pair of air-permeable and liquid-resistant barrier flaps formed on a pair of transversely opposite side flaps so as to elastically extend in a longitudinal direction of the diaper.

Japanese Patent Publication Gazette (Kokai) No. Hei4-55072 discloses a method for making a backsheet used in a disposable diaper, particularly to obtain such backsheet made of an air-permeable and liquid-impermeable plastic film.

In these Gazettes, the term "air-permeable and liquid-resistant" and the term "air-permeable and liquid-impermeable" are synonymously used. These known techniques may be adopted to improve a ventilation property of the foregoing barrier flaps and portions of a diaper backsheet in the proximity of the barrier flaps intended to surround the wearer's legs and thereby to alleviate undesirable stuffiness during use of the diaper.

The diaper proposed by the above-mentioned techniques will necessarily enlarge a diameter of each aperture formed in the barrier flaps and/or the backsheet in order to improve the air-permeability in these barrier flaps and/or backsheet. However, such measure may cause the desirable liquid-impermeability required for the barrier flaps and/or the backsheet. In other words, the conventional techniques have an antimonic relationship between improvement of the air-permeability and improvement of the liquid-impermeability.

SUMMARY OF THE INVENTION

In view of the problem as has been described above, it is an object of the invention to provide a disposable diaper having both a relatively high air-permeability and a relatively high liquid-impermeability.

In an embodiment, a disposable diaper comprises a liquid-permeable topsheet, a liquid-impermeable backsheet and a liquid-absorbent core disposed therebetween so as to form a front waist region, a rear waist region and a crotch region extending therebetween. Longitudinally opposite front and rear end flaps and transversely opposite side flaps are formed by portions of the topsheet and backsheet that extend outward from peripheral edges of the absorbent core. A pair of barrier cuffs, which are elastically extendable in a longitudinal direction of the diaper, are bonded, in an extended condition, to an inner surface of an associated one of the side flaps. Each of the barrier cuffs has longitudinally opposite front and rear ends, and inner and outer side edges extending in parallel to each other between the front and rear ends. The front and rear ends of each of the barrier cuffs are respectively bonded to the front and rear end flaps. Each of the barrier cuffs has, in the crotch region, the outer side edge bonded to the associated side flap and the inner side edge bonded to the associated side flap along a line defined between the outer side edge and an associated edge of the absorbent core. Each of the barrier cuffs has, in a transverse cross-sectional view and in the crotch region, (1) a first wall section formed with a plurality of elastic members and which first wall section extends inwardly from the outer side edge of the barrier cuff, an outermost one of the elastic members being spaced and distinct from the bonding of the outer side edge of the barrier cuff and the associated side flap, and (2) a second wall section intersecting the first wall section inwardly of an innermost one of the elastic members and extending downward to the inner side edge of the barrier cuff. A dimension of the first wall section in a transverse direction thereof is larger than that of the second wall section in the transverse direction. The first and second wall sections, together with a portion of the associated side flap defined between the outer and inner side edges, describe a hollow space of a substantially triangular shape, under contraction of the barrier cuff in the longitudinal direction. Portions of the barrier cuffs and the side flaps participating in the formation of the triangular hollow spaces are air-permeable. An outer longitudinally extending edge of the backsheet terminates beneath the inner side edge of one of the barrier cuffs and is adhesively attached to an extension sheet having an inner edge at the area of attachment and an outer edge. The extension sheet extends transversely from the inner edge outward and is attached to the one of the barrier cuffs at the outer edge thereof. The elastic members include at least three elastic members, the innermost elastic member has an extension stress less than an extension stress of the outermost elastic member, and an extension stress of the elastic member or members disposed between the innermost and outermost elastic members is equal to or less than the extension stress of the innermost elastic member. The extension stress of the elastic member or members disposed between the innermost and outermost elastic members is less than the extension stress of the innermost elastic member.

In a further embodiment, a disposable diaper comprises a liquid-permeable topsheet, a liquid-impermeable backsheet and a liquid-absorbent core disposed therebetween so as to form a front waist region, a rear waist region and a crotch region extending therebetween. Longitudinally opposite front and rear end flaps and transversely opposite side flaps are formed by portions of the topsheet and backsheet that extend outward from peripheral edges of the absorbent core. A pair of barrier cuffs, which are elastically extendable in a longitudinal direction of the diaper, are bonded, in an extended condition, to an inner surface of an associated one of the side flaps. Each of the barrier cuffs has longitudinally opposite front and rear ends, and inner and outer side edges extending in parallel to each other between the front and rear ends. The front and rear ends of each of the barrier cuffs are respectively bonded to the front and rear end flaps. Each of the barrier cuffs has, in the crotch region, the outer side edge bonded to the associated side flap and the inner side edge bonded to the associated side flap along a line defined between the outer side edge and an associated edge of the absorbent core. Each of the barrier cuffs has, in a transverse cross-sectional view and in the crotch region, (1) a first wall section formed with a plurality of elastic members and which first wall section extends inwardly from the outer side edge of the barrier cuff, an outermost one of the elastic members being spaced and distinct from the bonding of the outer side edge of the barrier cuff and the associated side flap, and (2) a second wall section intersecting the first wall section inwardly of an innermost one of the elastic members and extending downward to the inner side edge of the barrier cuff. A dimension of the first wall section in a transverse direction thereof is larger than that of the second wall section in the transverse direction. The first and second wall sections, together with a portion of the associated side flap defined between the outer and inner side edges, describe a hollow space of a substantially triangular shape, under contraction of the barrier cuff in the longitudinal direction. Portions of the barrier cuffs and the side flaps participating in the formation of the triangular hollow spaces are air-permeable. The topsheet is bonded to the inner side edges of the barrier cuffs along bonding lines and terminated at the bonding lines without further extending into the hollow spaces. An air-permeability of the backsheet in portions thereof participating in the formation of the hollow spaces is about same as in a remainder of the backsheet which does not participate in the formation of the hollow spaces. The elastic members include at least three elastic members, the innermost elastic member has an extension stress less than an extension stress of the outermost elastic member, and an extension stress of the elastic member or members disposed between the innermost and outermost elastic members is less than the extension stress of the innermost elastic member.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description thereof are to be regarded as illustrative in nature, and not as restrictive.

BRIEF DESCRIPTION OF THE DRAWINGS

FIG. 5 is a partial view similar to FIG. 2 showing alternative embodiments of the diaper according to the invention.

DESCRIPTION OF THE PREFERRED EMBODIMENTS

Details of a disposable diaper provided according to the invention will be more fully understood from the following description with reference to the accompanying drawings.

Figure 1:
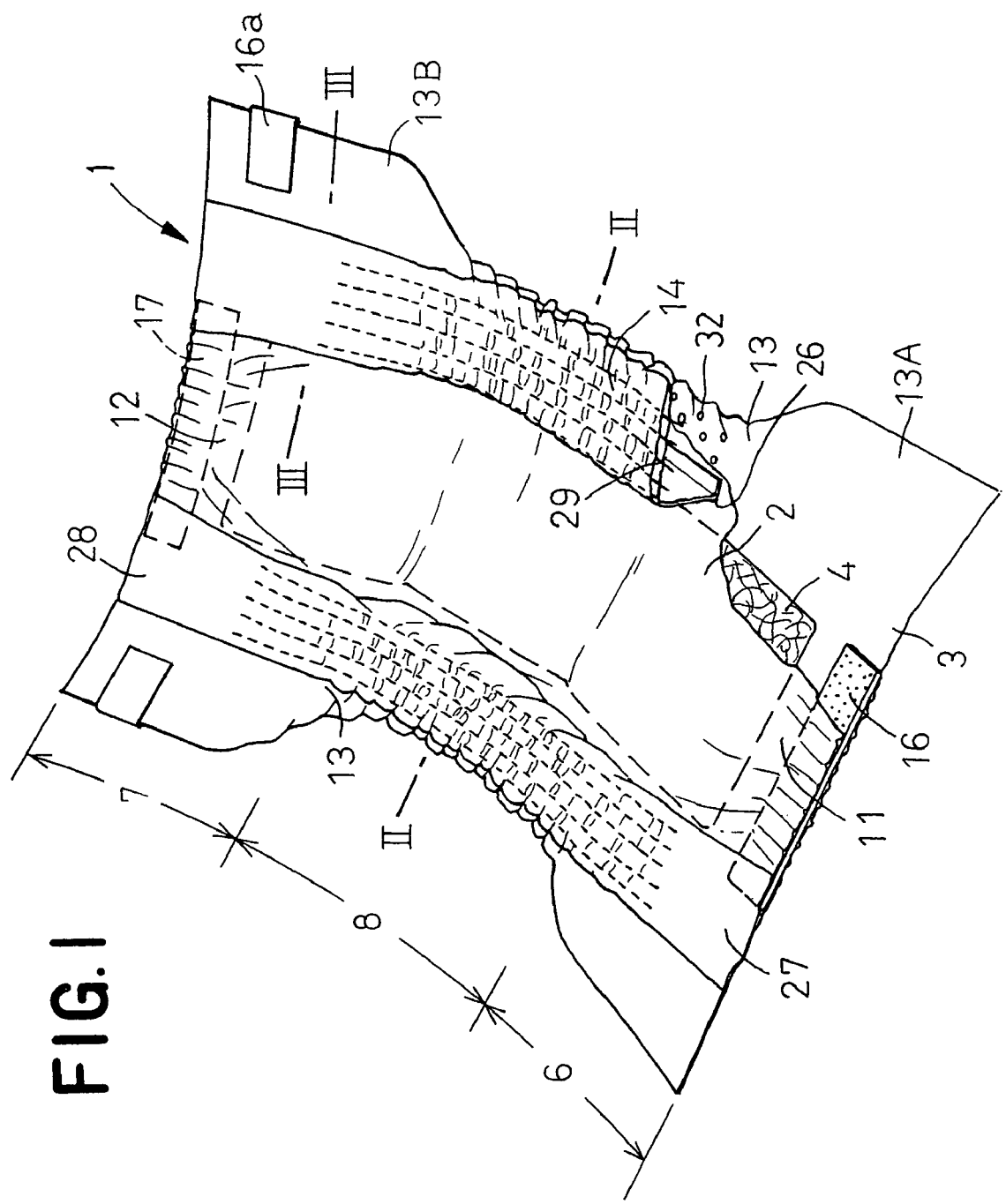
FIG. 1 is a perspective view showing an embodiment of a disposable diaper according to the invention as partially broken away.

Disposable diaper 1 shown by FIG. 1 in a perspective view as partially broken away comprises a liquid-permeable topsheet 2, a liquid-impermeable backsheet 3 and a liquid-absorbent core 4 disposed between these two sheets 2, 3. The sheets 2, 3 and absorbent core 4 forms a front waist region 6, a rear waist region 7 and a crotch region 8 longitudinally extending between these two regions 6, 7. The absorbent core 4 is in a shape of rectangle or hourglass which is relatively larger longitudinally of the diaper 1. Portions of the topsheet 2 and the backsheet 3 extending outward beyond peripheral edges of the absorbent core 4 are placed upon each other and bonded together by means of hot melt adhesive (not shown) so as to form longitudinally opposite front and rear end flaps 11, 12 and transversely opposite side flaps 13. In the front and rear waist regions 6, 7, each of the side flaps 13 extend outward to form front and rear wings 13A, 13B, respectively. Each of the side flaps 13 is formed on an inner surface thereof with a barrier cuff 14 extending along the crotch region 8 and partially into the front and rear waist regions 6, 7. The barrier cuff 14 is provided with a plurality of elastic members 29 extending longitudinally thereof. The front and rear end flaps 11, 12 are provided between the topsheet 2 and the backsheet 3 with elastic members 16, 17 extending circumferentially of the respective waist regions 6, 7. The elastic members 16, 17 are secured, in an extended condition, to an inner surface of at least one of the topsheet 2 and the backsheet 3. A pair of tape fasteners 16a are attached to the respective wings 13B of the rear waist region 7 in the vicinity of side edges thereof.

Figure 2:
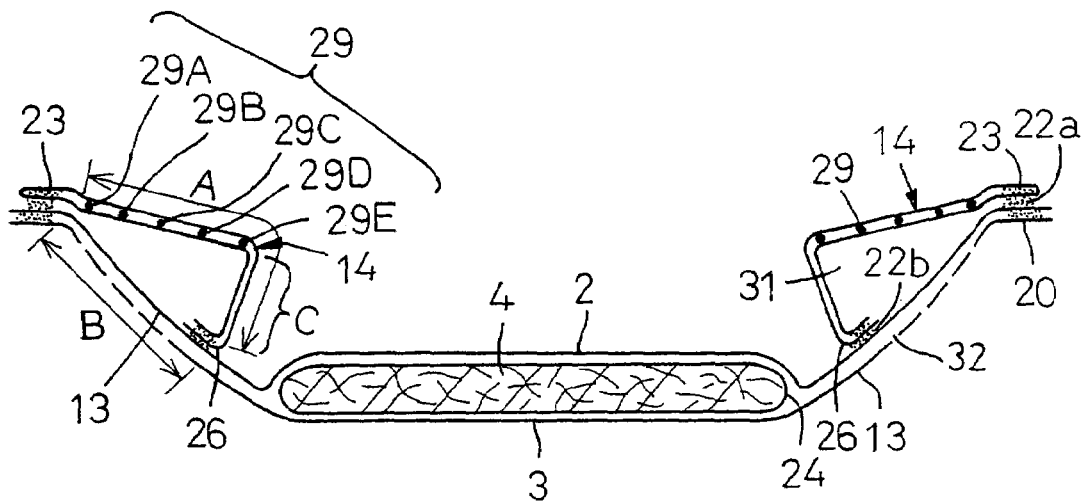
FIG. 2 is a sectional view taken along a line II—II in FIG. 1.

FIG. 2 is a sectional view taken along a line II—II in FIG. 1. The barrier cuff 14 is made of an air-permeable sheet and comprises, as seen transversely of the diaper 1, an outer side edge 23 bonded to an inner surface of the side flap 13 along an outer edge 20 thereof by means of hot melt adhesive 22a and an inner side edge 26 bonded to an inner surface of the side flap 13 with adhesive 22b along an intermediate zone between the outer side edge 23 and a side edge 24 of the absorbent core 4. The barrier cuff 14 further comprises longitudinally opposite front and rear ends 27, 28 (See FIG. 1) bonded to the respective end flaps 11, 12 of the front and rear waist regions 6, 7. The barrier cuff placed upon the side flap 13 has a plurality of elastic members 29 secured, in an extended condition in the longitudinal direction, to the inner surface of the side flap 13 by means of hot melt adhesive (not shown).

The barrier cuff 14 has a transverse dimension A between the outer and inner side edges 23, 26 and the side flap 13 has a transverse dimension B similarly between the two side edges 23, 26. The dimension A is preferably 1.2~2.0 times, more preferably 1.3~1.7 times of the dimension B which is, in turn, preferably in a range of 15~90 mm. Referring to FIG. 2, the elastic members 29 of the barrier cuff 14 are designated by reference numerals 29A~29E. Of the elastic members 29A~29E, the outermost elastic member 29A longitudinally extending adjacent the outer side edge 23 has the highest extension stress and the innermost elastic member 29E longitudinally extending between the outer side edge 23 and the inner side edge 26 has an extension stress equal to or less than the extension stress of the elastic member 29A. The elastic members 29B~29D interposed between the two elastic members 29A, 29E respectively have an extension stress equal to or less than the extension stress of the elastic member 29E. The number of the elastic members 29B,~29D to be interposed between the elastic members 29A, 29E is not limited to the number used in the embodiment of FIG. 2 and may be selectively increased or decreased without departing from the scope of the invention. When the diaper 1 is inwardly curved along a longitudinal axis thereof with the topsheet inside as shown in FIG. 1, contraction of the elastic members 29 causes the inner surface of the barrier cuff 14 to be moved away from the inner surface of the side flap 13. Consequently, the barrier cuff 14 cooperates with the side flap 13 to form a hollow space 31. In a state of the barrier cuff 14 having thus formed the hollow space 31, a wall section of the barrier cuff 14 defined between the elastic member 29A and the elastic member 29E is substantially flat and a wall section C of the barrier cuff 14 defined between the elastic member 29E and the inner side edge 26 is forced by the absorbent core 4 to extends downward because the absorbent core 4 is lowered as the diaper 1 is curved inwardly. The side flap 13 extends obliquely between the outer side edge 23 and the inner side edge 26 of the barrier cuff 14, as seen in FIG. 2.

The barrier cuff 14 serving as an important component of the hollow space 31 comprises the air-permeable sheet as previously mentioned. On the other hand, the backsheet 3 is formed with a plurality of air-permeable apertures 32 and the topsheet 2 placed upon the backsheet 3 is also air-permeable and liquid-permeable. Thus, a portion of the side flap 13 serving as another component of the hollow space 31 and comprising the topsheet 2 and the backsheet 3 is also air-permeable. Accordingly, the substantially entire peripheral wall defining the hollow space 31 is air-permeable.

Figure 3:
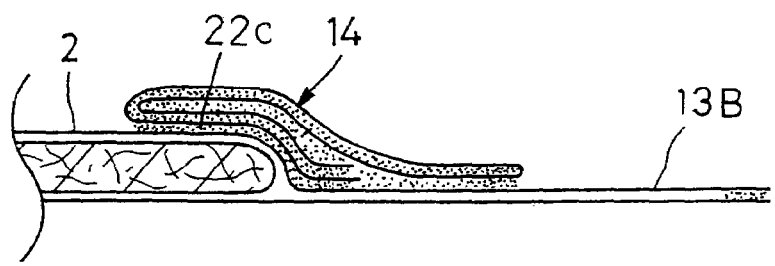
FIG. 3 is a sectional view taken along a line III—III in FIG. 1.

FIG. 3 is a sectional view taken along a line III—III in FIG. 1. As shown, the hollow space 31 is collapsed in the vicinity of the longitudinal ends of the front and rear waist regions 6, 7, respectively. In the vicinity of the longitudinal ends of the front and rear region 6, 7, the barrier cuff 14 is bonded to the upper surface of the topsheet 2 and, at the same time, layers of the barrier cuff 14 folded one upon another are bonded together by means of hot melt adhesive 22c.

With the diaper 1 of such construction being put on a wearer, the relatively flat wall of the barrier cuff 14 extending between the elastic member 29A and the elastic member 29E is normally placed against a crotch zone or around the legs of the wearer. In this state, the wall section C and the side flap 13 of the barrier cuff 14 extend downward so as to cooperate with the relatively flat wall to define the hollow space 31. Depending on a posture taken by the wearer, the absorbent core 4 may move upward into close contact with the wearer's crotch zone, collapsing the hollow space 31 and thereby decreasing its inner volume. However, the hollow space 31 restores again to its full inner volume shown in FIG. 2 as the absorbent core 4 downward moves away from the wearer's crotch zone. As the inner volume of the hollow space 31 decreases, vapor-containing air staying within the hollow space 31 as well as stuffy air in the diaper 1 is expelled to the exterior through the air-permeable barrier cuff 14 and the air-permeable side flap 13. On the contrary, as the inner volume of the hollow space 31 increases, external dry air is sucked through the barrier cuff 14 and the side flap 13 to the interior of the diaper 1.

With such diaper 1, an amount of body fluids flowing sideways over the crotch region 8 is blocked by the barrier cuff 14. Even if the amount of body fluids flowing sideways has partially penetrated the barrier cuff 14 into the hollow space 31, such amount of body fluid is then prevented by the side flap 13 from further flowing sideways to the exterior of the diaper 1. In this manner, the amount of body fluids which otherwise might leak sideways over the crotch region 8 can be double-blocked and this feature allows air-permeability of the barrier cuff 14 as well as of the side flap 13 to be adjusted to a relatively high value.

Figure 4:
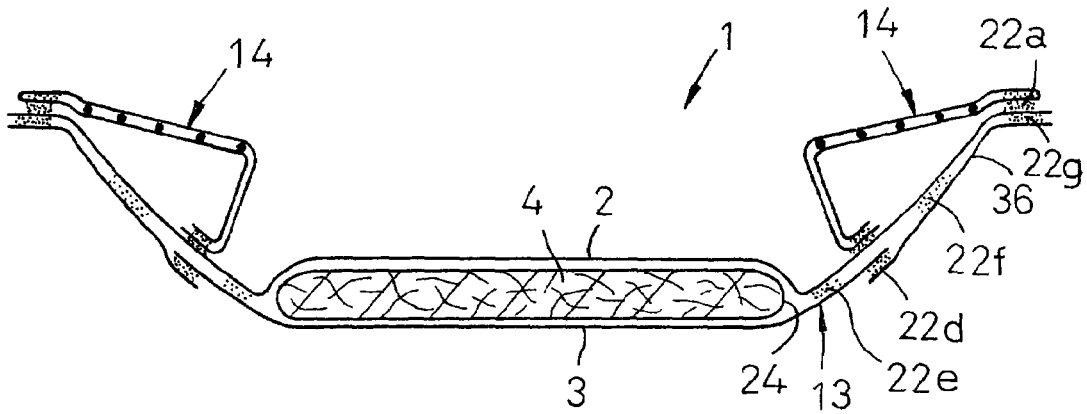
FIG. 4 is a view similar to FIG. 2

FIG. 4 is a view similar to FIG. 2 showing an alternative embodiment of the invention. The embodiment of FIG. 4 is similar to that of FIG. 2 except as to a configuration of its side flaps 13. The side flap 13 shown in FIG. 4 comprises the topsheet 2 largely extending beyond the side edge 24 of the absorbent core 24, the backsheet 3 slightly extending beyond the side edge 24, and an extension sheet 36 bonded to an outer end of the extended backsheet 3 by means of hot melt adhesive 22d. The topsheet 2, backsheet 3 and extension sheet 36 are placed one upon another and/or overlapped one by another and bonded together along predetermined zones utilizing lines of hot melt adhesive 22e, 22f, 22g. Each extension sheet 36 extends not only along the side edge of the crotch region 8 but also along respective side edges of the front and rear waist regions 6, 7 to their longitudinal ends. Preferably, the extension sheet 36 has an air-permeability higher than that of the backsheet 3.

To exploit the invention, a liquid-permeable nonwoven fabric or a liquid-permeable apertured plastic sheet may be employed as material for the topsheet 2. Such nonwoven fabric preferably has a basis weight of 10~50 g/m$^2$. The backsheet 3 is made of a plastic sheet, more preferably of air-permeable and liquid-permeable plastic sheet. The portion of the backsheet 3 participating in formation of the hollow space 31 may be formed with a plurality of apertures 32 each having a diameter of 0.1~2 mm at a total aperture area ratio of 2~10% with respect to an entire area of the aforesaid portion in order to improve its air-permeability. The air-permeable sheet as the important component of the barrier cuff 14 may be made of an air-permeable nonwoven fabric having a basis weight of 10~100 g/m$^2$. The barrier cuff 14 may be double-layered as in the embodiments shown, but the barrier cuff 14 may be realized also in the form of a single-layered sheet. According to the embodiments shown, the portions of the topsheet 2 and the backsheet 3 participating in formation of the hollow space 31 are placed upon each other. Such arrangement ensures that, even if the apertures 32 of the backsheet 3 are of relatively large diameter, body fluids can be effectively prevented from leaking through the apertures 32. If it is unnecessary to provide the backsheet 3 with those apertures 32 for improvement of its air-permeability, the topsheet 2 may be bonded to the inner side edge 26 of the barrier cuff 14 and terminated at this bonding line without further extending into the hollow space 31, as shown in FIG. 5. Nonwoven fabrics employed as material for the topsheet 2, the backsheet 3 and the extension sheet 36 may be locally treated to provide them with hydrophilic or hydrophobic nature, so far as they have zones requiring such treatment.

What is claimed is:

1. A disposable diaper, comprising:
   a liquid-permeable topsheet, a liquid-impermeable backsheet and a liquid-absorbent core disposed therebetween so as to form a front waist region, a rear waist region and a crotch region extending therebetween;
   longitudinally opposite front and rear end flaps and transversely opposite side flaps which are formed by portions of said topsheet and backsheet that extend outward from peripheral edges of said absorbent core;
   a pair of barrier cuffs being elastically extendable in a longitudinal direction of said diaper and being bonded, in an extended condition, to an inner surface of an associated one of said side flaps;
   each of said barrier cuffs having longitudinally opposite front and rear ends, and inner and outer side edges extending in parallel to each other between said front and rear ends;
   said front and rear ends of each of said barrier cuffs being respectively bonded to said front and rear end flaps;
   each of said barrier cuffs having, in said crotch region, said outer side edge bonded to said associated side flap and said inner side edge bonded to said associated side flap along a line defined between said outer side edge and an associated edge of said absorbent core; and
   each of said barrier cuffs having, in a transverse cross-sectional view and in the crotch region,
   a first wall section formed with a plurality of elastic members and which first wall section extends inwardly from the outer side edge of said barrier cuff, an outermost one of said elastic members being spaced and distinct from said bonding of the outer side edge of said barrier cuff and the associated side flap, and a second wall section intersecting the first wall section inwardly of an innermost one of said elastic members and extending downward to the inner side edge of said barrier cuff;

wherein a dimension of said first wall section in a transverse direction thereof is larger than that of said second wall section in said transverse direction;

said first and second wall sections, together with a portion of said associated side flap defined between said outer and inner side edges, describe a hollow space of a substantially triangular shape, under contraction of said barrier cuff in the longitudinal direction;

portions of said barrier cuffs and said side flaps participating in the formation of said triangular hollow spaces are air-permeable;

an outer longitudinally extending edge of the backsheet terminates beneath the inner side edge of one of the barrier cuffs and is adhesively attached to an extension sheet having an inner edge at the area of attachment and an outer edge, and which extension sheet extends transversely from the inner edge outward and is attached to said one of the barrier cuffs at the outer edge thereof;

said plurality of elastic members include at least three elastic members, the innermost elastic member has an extension stress less than an extension stress of the outermost elastic member, and an extension stress of the elastic member or members disposed between the innermost and outermost elastic members is equal to or less than the extension stress of the innermost elastic member; and the extension stress of the elastic member or members disposed between the innermost and outermost elastic members is less than the extension stress of the innermost elastic member.

2. The diaper of claim 1, wherein the extension sheet has an air-permeability higher than that of the backsheet.

3. A disposable diaper, comprising:

a liquid-permeable topsheet, a liquid-impermeable backsheet and a liquid-absorbent core disposed therebetween so as to form a front waist region, a rear waist region and a crotch region extending therebetween;

longitudinally opposite front and rear end flaps and transversely opposite side flaps which are formed by portions of said topsheet and backsheet that extend outward from peripheral edges of said absorbent core;

a pair of barrier cuffs being elastically extendable in a longitudinal direction of said diaper and being bonded, in an extended condition, to an inner surface of an associated one of said side flaps;

each of said barrier cuffs having longitudinally opposite front and rear ends, and inner and outer side edges extending in parallel to each other between said front and rear ends;

said front and rear ends of each of said barrier cuffs being respectively bonded to said front and rear end flaps;

each of said barrier cuffs having, in said crotch region, said outer side edge bonded to said associated side flap and said inner side edge bonded to said associated side flap along a line defined between said outer side edge and an associated edge of said absorbent core; and each of said barrier cuffs having, in a transverse cross-sectional view and in the crotch region, a first wall section formed with a plurality of elastic members and which first wall section extends inwardly from the outer side edge of said barrier cuff, an outermost one of said elastic members being spaced and distinct from said bonding of the outer side edge of said barrier cuff and the associated side flap, and a second wall section intersecting the first wall section inwardly of an innermost one of said elastic members and extending downward to the inner side edge of said barrier cuff;

wherein a dimension of said first wall section in a transverse direction thereof is larger than that of said second wall section in said transverse direction;

said first and second wall sections, together with a portion of said associated side flap defined between said outer and inner side edges, describe a hollow space of a substantially triangular shape, under contraction of said barrier cuff in the longitudinal direction;

portions of said barrier cuffs and said side flaps participating in the formation of said triangular hollow spaces are air-permeable;

said topsheet is bonded to the inner side edges of said barrier cuffs along bonding lines and terminated at said bonding lines without further extending into the hollow spaces;

an air-permeability of said backsheet in portions thereof participating in the formation of said hollow spaces is about same as in a remainder of said backsheet which does not participate in the formation of said hollow spaces; and said plurality of elastic members include at least three elastic members, the innermost elastic member has an extension stress less than an extension stress of the outermost elastic member, and an extension stress of the elastic member or members disposed between the innermost and outermost elastic members is less than the extension stress of the innermost elastic member.

* * * * *